United States Patent [19]
Villanueva et al.

[11] Patent Number: 5,733,851
[45] Date of Patent: Mar. 31, 1998

[54] FORMULATION AND PROCEDURE TO INCREASE RESISTANCE OF PLANTS TO PATHOGENIC AGENTS AND ENVIRONMENTAL STRESS

[76] Inventors: Jaime Villanueva, Moneda 920, Oficina 507, Santiago, Chile; Pablo D.T. Valenzuela, 2919 Avalon, Berkeley, Calif. 94705

[21] Appl. No.: 713,395

[22] Filed: Sep. 13, 1996

Related U.S. Application Data

[60] Provisional application No. 60/003,749, Sep. 14, 1995.
[51] Int. Cl.$^6$ .................................................. A01N 43/16
[52] U.S. Cl. ............................................. 504/292; 514/55
[58] Field of Search ............................... 504/292; 514/55

[56] References Cited

U.S. PATENT DOCUMENTS

| | | | |
|---|---|---|---|
| 4,812,159 | 3/1989 | Freepons | 71/16 |
| 4,886,541 | 12/1989 | Hadwiger | 71/77 |
| 5,374,627 | 12/1994 | Ito et al. | 514/55 |

*Primary Examiner*—S. Mark Clardy
*Attorney, Agent, or Firm*—Evenson, McKeown, Edwards & Lenahan, PLLC

[57] ABSTRACT

Methods and compositions for treating the root system of seedlings, young plants, and plants at whatever stage of development. Examples of the plants to be treated includes forestry species, horticultural species, floricultural species, and other important agricultural crops. Such treatment enhances plant resistance to pests and survival in adverse environmental conditions. The results include significant overall improvements in growth and yield of said forestry, horticultural, and other crops.

18 Claims, No Drawings

FORMULATION AND PROCEDURE TO INCREASE RESISTANCE OF PLANTS TO PATHOGENIC AGENTS AND ENVIRONMENTAL STRESS

This application claims priorty under 35 USC 119(e) of US Provisional Application SN 60/003749 filed Sep. 14, 1995.

FIELD OF THE INVENTION

This invention pertains to methods and compositions for treating the root system of seedlings, young plants, and plants at whatever stage of development. Examples of the plants to be treated includes forestry species, horticultural species, floricultural species, and other important agricultural crops. Such treatment enhances plant resistance to pests and survival in adverse environmental conditions. The results include significant overall improvements in growth and yield of said forestry, horticultural, and other crops.

BACKGROUND OF THE INVENTION

Crop protection plays a vital and integral role in modern-day agricultural production. The increasing demands on yield and the projected shortfall in production relative to demand has led to an optimization of farming practices worldwide. The attempt to meet increased demand has increased the potential for pest damage and the need for pest control.

Plants possess a wide variety of mechanisms for protecting themselves against infection due to pathogenic microorganisms. These defense systems involve natural barriers present in the cell wall that inhibit microbial penetration. Examples of cell wall barriers include lignin, tannins, phenols, and cellulose.

Presently, however, crop protection in such agricultural systems relies almost exclusively on the use of agrochemicals. The use of chemical pesticides results in the rapid build-up of plant resistance to such compounds. Also, the non-selectivity of the pesticides adversely affects the balance between the plant's pests and the natural predators, in favor of the pests. Thus, there still remains the need to provide a greater and more efficient method of protection to crops. An estimated 37% of all crop production is lost world wide to pests and diseases. In addition, because of ecological concerns and the growing commercial importance of organic agriculture there is a growing demand for natural, non-toxic and biodegradable products.

Plants lack an immune system, but have evolved an active defense system which involves the activation of host defense genes. The activation of plant defense genes can result in physical and biochemical changes. For example, the properties of the plant cell wall can change. Examples include accumulation of hydroxyproline-rich glycoproteins (Esquerre-Tugaye, M. T., Lafitte, C., Mazau, D., Toppan, A., and Tonze, A., Plant Physiol. 64, 320–326 (1979); Showalter, A. M., Bell, J. N., Craver, C. L., Bailey, J. A., Varner, J. E., and Lamb, C. L, Proc. Natl. Acad. Sci. USA 82, 6551–6555 (1985)), signification and suberization (Vance, C. P., Kirk, T. K., and Sherwood, R. T., Espelie, K. E., Francheschi, V. R., and Kolattukudy, P. E.; Plant Physiol. 81, 487–492 (1986)), callous deposition (Ride, J. P.; In Biochemical Plant Pathology (Ed. J. A. Callow); John Wiley & Sons, New York, pp. 215–236 (1983), Bonhoff, A., Reith, B., Golecki, J., and Grisebach, H.; Planta 172, 101–105 (1987)) and the accumulation of phenolic compounds Matta, A., Gentile, H., and Giai, L.; Phytopathol., 59, 512–513 (1969); Hunter, R. L., Physiol. Plant Pathol. 4, 151–159 (1974)). Also, activation of defense systems can lead to biosynthesis and accumulation of phytoalexins and anti-microbial compounds not present in healthy plants which accumulate in response to microbial infection and are toxic to bacteria and fungi (Bell, A. A.; Ann. Rev. Plant Physiol. 32, 21–81 (1981); Darvill, A. G. and Albersheim, P.; Ann. Rev. Plant Physiol. 35, 243–275 (1984); Hahlbrock, K. and Grisebach, H.; Ann. Rev. Plant Physiol. 30, 105–130 (1979); Dixon, R. A., Day, P. M., and Lamb, C. J.; Adv. Enzymol. 55, 1–136 (1983)), the accumulation of protease inhibitors (Bell, A. A.; Ann. Rev. Plant Physiol. 32, 21–81 (1981); Ryan, C. A.; Ann. Rev. Plant Physiol. 24, 173–196 (1973); Peng, F. H., and Black, L. L.; Phytopathol. 66, 958–963 (1976)) and the release of oligosaccharide elicitors of plant origin (Albersheim, P.; Nato ASI Series, Springer Verlag p. 380 (1981)). In addition, in response to pathogen attack, plants also accumulate a novel class of proteins termed "pathogenesis-related proteins" or PR-proteins, in response to pathogen attack. (Van Leon, L. C.; Plant Mol. Biol. 4, 111–116 (1985); Bol. J., Linthorst, H., and Cornelissen; Ann. Rev. Phytopathol. 28, 113–138 (1990); Linthorst, H.; Critical Reviews in Plant Sciences 10, 123–150 (1991); Bowles, D. J.; Ann. Rev. Biochem. 59, 873–907 (1990)).

The lyric enzymes chitinase and $\beta$-1,3-glucanase are among the antimicrobial compounds induced against fungal pathogens. These enzymes digest chitin and glucosamine, major constituents of the cell wall of a number of fungal pathogens. (See, for example, Bol et al., Ann. Rev. Phytopathol. 28:113–138 (1990); Linthorst, Critical Reviews in Plant Sciences 10:123–150 (1991); and Bowles, Ann. Rev. Biochem. 59:873–907 (1990)).

These enzymes may also be involved in plant resistance in insect attacks because chitin is present in the exoskeleton of insects. The fragments that result from this enzymatic cleavage may elicit host stress metabolite biosynthesis. Thus, these enzymes appear to be involved in host signaling as well as pathogen degradation (Ryan, Ann. Rev. Cell Biol. 3:295–317 (1987); Mauch et al., Plant. Cell. 1:447–456 (1989); Lamb et al., Cell 56:215–220 (1989)).

The present invention offers a formulation comprising an effective amount of chitosan, which after application to the root system of plants enhances the plant's resistance to pathogenic fungi and, as a consequence, increases plant survival and growth.

Formulations and procedures have been developed to coat seeds with a film of chitosan. See PCT WO89/01288. The present invention discloses a different chitosan formulation to be applied by immersing the roots of the plants directly in the formulation before planting or by irrigating the plants after planting. These formulations and methods have not been considered previously and are very effective in increasing plant resistance to pathogenic agents as well as to adverse environmental conditions.

SUMMARY OF THE INVENTION

The object of the invention is to provide a formulation comprising chitosan, a polymer of $\beta$1,4 glycosamine, which enhances plant resistance to pathogenic fungi and other microbial pathogens such as bacteria and other arthropod pathogens such as insects when contacted to the roots of plants. In addition, the formulation enhances the plant resistance to other adverse environmental conditions such as drought, salinity, excessive wind, poor soil, etc. The formulation comprises:

(a) chitosan exhibiting a viscosity from about 150 cps to 350 cps and exhibiting a degree of deacetylation of 50% to 80%;

(b) a weak acid in a concentration from about 1% to 10% (volume/volume);

(c) an effective amount of chitosan from about 0.30 to 0.75% (weight/volume); wherein the pH of said formulation is from about 3.5 to 6.5.

Another object of the invention relates to a method of formulating chitosan as a solution:

(a) providing a chitosan composition exhibiting a viscosity from about 150 cps to 350 cps and exhibiting a degree of deacetylation of 50% to 80%;

(b) providing a weak acid in a concentration from about 1% to 10% (volume/volume);

(c) dissolving the chitosan composition in the weak acid solution that results in a solution comprising chitosan at a concentration from about 8 to 12 mg/ml;

(d) adjusting the pH of the solution to about 3.5 to 6.5;

(e) adding water to solution to adjust the chitosan to a final concentration from about 0.3% to about 0.75% (weight/volume).

Yet another object of the invention relates to a method to increase plant resistance to pathogenic agents as well as other adverse environmental conditions (dryness, wind, salinity, poor soil, etc.) by contacting a formulation comprising an effective amount of chitosan to the root system of a plant. The method comprises:

(a) providing a chitosan formulation comprising:
   (i) chitosan exhibiting a viscosity from about 150 cps to 350 cps and exhibiting a degree of deacetylation of 50% to 80%;
   (ii) a weak acid in a concentration from about 1% to 10% (volume/volume);
   (iii) an effective amount of chitosan from about 0.30 to 0.75% (weight/volume);
wherein the pH of said formulation is from about 3.5 to 6.5;

(b) contacting the roots of the plant with a sufficient amount of the chitosan formulation to moisten substantially all the surface of the roots before planting;

(c) transplanting the plant immediately after step (b);

(d) alternatively contacting the roots of the plant with a sufficient amount of chitosan formulation by irrigation after the plant is transplanted.

Yet another object of the invention relates to a method to increase plant resistance to pathogenic agents as well as other adverse environmental conditions (dryness, wind, salinity, poor soil, etc.) by contacting a formulation such as those previously described but which can be diluted to fit particular needs of the plants, presence of specific pathogens or specific environmental conditions.

DETAILED DESCRIPTION

Definitions

An effective amount of chitosan refers to an amount which at a concentration of 8–12 mg/ml substantially covers the surface of the roots. Typically, an effective amount of chitosan is one that at the concentration of 8–12 mg/ml is able to increase the mass of roots and/or the diameter of the stem and/or the height of the plant each by at least 10%.

The physico-chemical characteristics of this formulation are such to obtain a maximal amount of active ingredient (chitosan) in a solution with sufficient viscosity to form a thin film around the surface of the roots but not so high as to form a thicker and stabler film which eventually suffocates the root and produces rotting.

The active ingredient of this formulation is chitosan which simulates a fungal attack on the plant. The plant reacts by several mechanisms, one of the most important is by increasing the mass of roots. A larger and stronger root system allows increased water intake and from deeper in the ground, increased nutrients intake and improved anchoring to the ground. These result in stimulation of growth, improved plant vigor and increased resistance to environmental stress.

A weak acid refers to an acid with a low dissociation constant, for example with a pKa of approximately 3 to 6. Examples of a weak acid include without limitation, acetic acid, adipic acid, citric acid, formic acid, lactic acid, malic acid, oxalic acid, piruvic acid, and tartaric acid.

GENERAL METHODS AND DETAILED DESCRIPTION

Chitosan, a polymer of $\beta$-1,4-glucosamine, is deacetylated chitin. Two characteristics of chitosan compositions are the degree of viscosity and the degree of deacetylation. The effectiveness of the chitosan formulation can be altered by choosing the desired degree of viscosity and degree of deacetylation.

The effectiveness of chitosan to increase plant resistance increases with the degree of polymerization. See Kauss et al., *Planta* 178:385–392 (1989). The degree of polymerization is typically measured by the viscosity of the chitosan composition. Preferably, the viscosity of the chitosan composition is at least 150 cps; more preferably 200 cps, even more preferably 250 cps. Typically, the viscosity will be no more than 300 cps; more typically no more than 350 cps.

Chitosan has been found to have a direct fungicidal activity. See Allan et al., *Exp. Mycol.* 3:285–287 (1979). In general, chitosan exhibits greater fungicidal activity than its acetylated form, chitin. Chitosan is significantly more soluble than chitin. Preferably, the degree of deacetylation of the chitosan composition is at least 50%; more preferably, 65%, even more preferably, 75%. Usually, the degree of deacetylation will be no more than 75%; more usually not more than 80%.

The optimal degree of viscosity and deacetylation will be chosen based on the plant to be treated. The characteristics can be varied and tested with the desired plants.

The physico-chemical characteristics of this formulation are such as to obtain a maximal amount of active ingredient (chitosan) in a solution with sufficient viscosity to form a thin film around the surface of the roots but not so high as to form a thicker and stabler film which eventually suffocates the root producing rotting.

Before adjusting the formulation to its final chitosan concentration, the chitosan composition is first dissolved into a weak acid solution. The weak acid to be used is chosen for convenience. Examples of weak acids include without limitation acetic acid, adipic acid, citric acid, formic acid, lactic acid, malic acid, oxalic acid, piruvic acid, and tartaric acid. Typically, the weak acid in solution is at a concentration of at least 1% (v/v); more typically, 3% (v/v); even more typically, 6% v/v. Usually, the concentration will be no more than 10% v/v; more usually no more than 8% v/v.

Preferably, the pH of the chitosan formulation is adjusted before adjusting the formulation to the final chitosan concentration. The pH is adjusted to a range that is well tolerated by plants. Preferably, the pH is at least 3.5; more preferably 6.2. Typically, the pH is no more than 6.4; more typically no more than 6.5. The pH can also be adjusted to prolong the shelf life of the formulation.

Preferably the final concentration of chitosan is 0.30% (w/v), more preferably 0.5% (w/v). Typically the concentration is no more than 0.75% (w/v), more typically no more than 0.6% (w/v).

The active ingredient of this formulation is chitosan which simulates a fungal attack on the plant. The plant reacts with several mechanisms, the most important of which is by increasing the mass of roots. A larger and stronger root system allows increased water intake and from deeper in the ground, increased nutrients intake and improved anchoring to the ground. These result in stimulation of growth, improved plant vigor and increased resistance to environmental stress.

Plants can be treated either by contacting the roots directly with the chitosan formulation by immersing the roots or by irrigating the plants.

When immersing the roots, substantially all the root surface contacts the chitosan formulation. Typically the time of immersion is 10 seconds, more typically 60 seconds and more usually no more than 30 seconds. Usually the time of immersion is no more than 5 minutes, more usually no more than 30 seconds. Preferably no less than 50% of the roots will be immersed, more preferably no less than 60%. Typically at least 70% of the roots are immersed and even more typically at least 80% of the roots are immersed. The plant is planted soon after contact with the chitosan formulation. Usually the plant is transplanted 10 minutes after immersion, more usually 5 minutes after immersion. Typically the plant is transplanted no more than 2 hours after immersion, even more typically no more than 30 minutes after immersion.

When irrigating the plants after planting, this operation is done within 30 minutes after planting, preferably within 20 minutes and more preferably within 10 minutes after planting. The volume of solution to be used depends on the size of the root system of the plant. Typically the volume is sufficient to irrigate 50% of the roots, more preferably 75% of the roots, even more preferably 100% of the roots.

When irrigating plants after planting and on an ongoing basis, this irrigation is done weekly, monthly, or at other intervals and with quantifies and dilutions depending on the level of activity of the plant.

The roots of a wide range of plants can be treated. Examples include without limitation to forestry species such as *Pinus radiata* and *Eucalyptus globulus*; horticulture plants such as tomatoes and asparagus and fruticultural plants such as but not limited to raspberries, blackberries, and blueberries; and floriculture plants such as but not limited to roses, gladioli, tulips, as well as interior or exterior decorative plants.

In general, applications of the invention include plants with a yearly or bi-annual life cycle as well as perennial plants.

What is claimed:

1. A chitosan formulation comprising:
   (a) chitosan exhibiting a viscosity from about 150 cps to 450 cps and exhibiting a degree of deacetylation of 50% to 80%;
   (b) a weak acid in a concentration from about 1% to 10% (volume/volume);
   (c) an effective amount of said chitosan for root treatment of plants, comprising from about 0.30 to 0.75% (weight/volume);
   wherein the pH of said formulation is from about 3.5 to 6.5.

2. The formulation of claim 1, wherein the chitosan exhibits a viscosity from about 200 to 250 cps and exhibits a degree of deacetylation from about 65 to 75%.

3. The formulation of claim 2, wherein the weak acid is selected from the group consisting of acetic acid, adipic acid, citric acid, formic acid, lactic acid, malic acid, oxalic acid, pyruvic acid, and tartaric acid.

4. The formulation of claim 3, wherein the formulation comprises bases selected from the group consisting of sodium hydroxide, sodium carbonate, and potassium hydroxide to adjust the pH.

5. A method of formulating chitosan as a solution for root treatment of plants to increase the resistance of plants to pathogenic agents comprising:
   (a) providing a chitosan composition exhibiting a viscosity from about 150 cps to 450 cps and exhibiting a degree of deacetylation from about 50% to 80%;
   (b) providing a weak acid solution exhibiting a concentration from about 1 to 10% (volume/volume);
   (c) dissolving the chitosan composition in the weak acid solution that results in a solution comprising chitosan at a concentration from about 8 to 12 mg/ml;
   (d) adjusting the pH of the solution to about 3.5 to 6.5;
   (e) adding water to solution to adjust the chitosan to a final concentration from about 0.30% to 0.75% (weight/volume).

6. The method of claim 5, wherein the weak acid is selected from the group consisting of acetic acid, adipic acid, citric acid, formic acid, lactic acid, malic acid, oxalic acid, pyruvic acid, and tartaric acid.

7. The method of claim 6, wherein the pH of the solution is adjusted with a base selected from the group consisting of sodium hydroxide, sodium carbonate, and potassium hydroxide.

8. A method of increasing the resistance of a plant to pathogenic agents or increasing the viability of a plant during dry periods, or other adverse environmental conditions, comprising:
   (a) providing a chitosan formulation comprising
      (i) chitosan exhibiting a viscosity from about 150 cps to 450 cps and exhibiting a degree of deacetylation of 50% to 80%;
      (ii) a weak acid in a concentration from about 1% to 10% (volume/volume); and
      (iii) an effective amount of chitosan from about 0.30 to 0.75% (weight/volume), wherein the pH of said formulation is from about 3.5 to 6.5;
   (b) immersing the roots of the plants with a sufficient amount of the chitosan formulation to moisten substantially all of the surface of the roots;
   (c) transplanting the plant soon after contacting with the formulation.

9. A method of increasing the resistance of a plant to pathogenic agents or increasing the viability of a plant during dry periods, or other adverse environmental conditions, comprising:
   (a) providing a chitosan formulation comprising
      (i) chitosan exhibiting a viscosity from about 150 cps to 450 cps and exhibiting a degree of deacetylation of 50% to 80%;
      (ii) a weak acid in a concentration from about 1% to 10% (volume/volume); and
      (iii) an effective amount of chitosan from about 0.30 to 0.75% (weight/volume), wherein the pH of said formulation is from about 3.5 to 6.5;
   (b) transplanting the plant;

(c) irrigating the plant with a sufficient amount of the chitosan formulation to moisten substantially all of the surface of the roots, at transplantation or planting time or during the life cycle of the plant.

10. The method of claim 9, wherein the plant is a forestry species, the roots are contacted with at least about 3 to 20 ml of the chitosan formulation.

11. The method of claim 10, wherein the genus of the plant is selected from the group consisting of Pinus, Eucalyptus, and Pseudotsuga.

12. The method of claim 9, wherein the plant is a horticultural crop, the roots are contacted with about 1 to 4 ml of the chitosan formulation.

13. The method of claim 12, wherein the horticultural crop is selected from the group consisting of tomato, peppers, asparagus, tobacco and coffee.

14. The method of claim 9, wherein the plant is a fruticultural crop and the roots are contacted with about 2 to 10 ml of the chitosan formulation.

15. The method of claim 14, wherein the fruticultural crop is selected, from the group consisting of apples, citrus, olives, raspberry, blackberry and blueberry.

16. The method of claim 9, wherein the plant is a floricultural crop and the roots are contacted with about 2 to 10 ml of the chitosan formulation.

17. The method of claim 16, wherein the floricultural crop is selected from the group consisting of roses, gladioli, tulips, and interior or exterior decorative plants.

18. The method of claim 9, wherein the plants to be treated comprise those with an annual, bi-annual or perennial life cycle.

* * * * *